US012558803B2

(12) United States Patent (10) Patent No.: US 12,558,803 B2
Hannaford et al. (45) Date of Patent: Feb. 24, 2026

(54) PASSIVE CONTROL SYSTEM FOR AN EVERTING SHEATH

(71) Applicant: University of Washington, Seattle, WA (US)

(72) Inventors: Blake Hannaford, Seattle, WA (US); Andrew Lewis, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 18/829,136

(22) Filed: Sep. 9, 2024

(65) Prior Publication Data

US 2025/0083339 A1 Mar. 13, 2025

Related U.S. Application Data

(60) Provisional application No. 63/537,724, filed on Sep. 11, 2023.

(51) Int. Cl.
| | |
|---|---|
| *B25J 18/06* | (2006.01) |
| *A61M 25/01* | (2006.01) |
| *B25J 9/14* | (2006.01) |
| *B25J 13/08* | (2006.01) |
| *B25J 19/00* | (2006.01) |
| *F03G 7/06* | (2006.01) |

(52) U.S. Cl.
CPC .............. *B25J 18/06* (2013.01); *B25J 9/142* (2013.01); *B25J 13/085* (2013.01); *B25J 19/0004* (2013.01); *F03G 7/064* (2021.08); *A61M 25/0119* (2013.01)

(58) Field of Classification Search
CPC . B25J 18/06; B25J 9/142; B25J 13/085; B25J 19/0004; F03G 7/064; A61M 25/0119
See application file for complete search history.

(56) References Cited

U.S. PATENT DOCUMENTS

| | | | | |
|---|---|---|---|---|
| 2003/0069628 A1* | 4/2003 | Solem | ..................... | A61F 2/958 623/1.11 |
| 2006/0079861 A1* | 4/2006 | Matasov | ............. | A61M 3/0287 604/540 |
| 2012/0059448 A1* | 3/2012 | Parker | ...................... | A61F 2/95 141/2 |

(Continued)

OTHER PUBLICATIONS

Berthet-Rayne, et al., "Mammobot: A Miniature Steerable Soft Growing Robot for Early Breast Cancer Detection", IEEE Robotics and Automation Letters, vol. 6, No. 3, Jul. 2021, pp. 5056-5063.

(Continued)

*Primary Examiner* — Hoang M Nguyen
(74) *Attorney, Agent, or Firm* — Stoel Rives LLP

(57) ABSTRACT

Apparatuses, systems, and methods are disclosed for regulating an eversion process in everting sheath systems to avoid uncontrolled deployment of the sheath. The sheath system includes a reel and a sheath stored thereon, where the sheath is capable of everting from a retracted position to an extended position as the reel rotates about a rotational axis. The rotational characteristics of the reel are controlled by a torque mechanism operable to directly or indirectly apply a passive torque to the reel to adjust a rate at which the sheath is released from the reel as the sheath everts from the retracted position to the extended position.

20 Claims, 5 Drawing Sheets

(56) References Cited

U.S. PATENT DOCUMENTS

| | | | |
|---|---|---|---|
| 2020/0245981 A1* | 8/2020 | Chin | ................. A61B 10/0291 |
| 2022/0322920 A1 | 10/2022 | Lewis et al. | |

OTHER PUBLICATIONS

Blumenschein, et al., "Design, Modeling, Control, and Application of Everting Vine Robots", Frontiers in Robotics and AI, vol. 7, Nov. 2020, pp. 1-24.

Brill, et al., "Resonance theory of elastic waves ultrasonically scattered from an elastic sphere", Journal of the Acoustical Society of America, vol. 81, 1987, pp. 1-21.

Camargo, et al., "Novel Everting Urologic Access Sheath: Potential Advantages of Decreased Cellular Advancement", Journal of Endourology, vol. 20 No. 2, 2006, pp. 153-156.

Coad, et al., "Retraction of Soft Growing Robots without Buckling", IEEE Robotics and Automation Letters, vol. 5, No. 2, 2020, pp. 2115-2122.

Coad, et al., "Vine Robots: Design, Teleoperation, and Deployment for Navigation and Exploration", IEEE Robotics Automation Magazine, vol. 27, No. 3, 2020, pp. 120-132.

Do, et al., "Dynamically Reconfigurable Discrete Distributed Stiffness for Inflated Beam Robots", IEEE International Conference on Robotics and Automation (ICRA), 2020, pp. 9050-9056.

Drew, et al., "Acoustic Communication and Sensing for Inflatable Modular Soft Robots", IEEE International Conference on Robotics and Automation, 2021, pp. 11827-11833.

Fichter, W.B., "A Theory for Inflated Thin-Wall Cylindrical Beams", Computer and Structures, vol. 3, No. 1, 1966, pp. 203-209.

Gao, et al., "Gated recurrent unit-based heart sound analysis for heart failure screening", BioMedical Engineering OnLine vol. 19, 01, 2020, pp. 1-17.

Greer, et al., "A Soft, Steerable Continuum Robot that Grows via Tip Extension", Soft Robotics vol. 6 No. 1, 2019, pp. 95-108.

Greer, et al., "Obstacle-Aided Navigation of a Soft Growing Robot", IEEE International Conference on Robotics and Automation (ICRA), vol. 2, 2018, pp. 4165-4172.

Greer, et al., "Series Pneumatic Artificial Muscles (sPAMs) and Application to a Soft Continuum Robot", IEEE International Conference on Robotics and Automation (ICRA), 2017, pp. 5503-5510.

Haggerty, et al., "Characterizing Environmental Interactions for Soft Growing Robots", IEEE/RSJ International Conference on Intelligent Robots and Systems (IROS), 2019, pp. 3335-3342.

Hawkes, et al., "A soft robot that navigates its environment through growth", Science Robotics vol. 2, No. 8, 2017, pp. 1-17.

Hwee, et al., "An Everting Emergency Airway Device", In 2021 International Symposium on Medical Robotics (ISMR), 2021, pp. 1-7.

Leonard, et al., "Structural Considerations of Inflatable Reentry Vehicles", NASA | Technical Note D-457, Sep. 1960, pp. 1-24.

Luong, et al., "Eversion and Retraction of a Soft Robot Towards the Exploration of Coral Reefs", 2nd IEEE International Conference on Soft Robotics (RoboSoft), 2019, pp. 801-807.

Rubenstein, et al., "Novel Everting Urologic Access Sheath: Decreased Axial Forces during Insertion", Journal of Endourology vol. 19, No. 10, Dec. 2005, pp. 1216-1220.

Runciman, et al., "Soft Robotics in Minimally Invasive Surgery", Soft Robotics | vol. 6, No. 4 | DOI: 10.1089/soro.2018.0136, 2019, pp. 423-443.

Rus, et al., "Design, fabrication and control of soft robots", Nature, vol. 521, No. 7553, 2015, pp. 467-475.

Saxena, et al., "Tubular Locomotion and Positioning Using Tip Eversion for Endoscopy", Journal of Medical Devices, Transactions of the ASME, vol. 14, No. 2, Jun. 2020, pp. 1-5.

Selvaggio, et al., "An obstacle-interaction planning method for navigation of actuated vine robots", IEEE International Conference on Robotics and Automation (ICRA), 2020, pp. 3227-3233.

Shewalkar, Apekshan., "Comparison of RNN, LSTM and GRU on Speech Recognition Data", Ph.D. dissertation, North Dakota State University, Oct. 2018, pp. 1-38.

Slade, et al., "Design of a Soft Catheter for Low-Force and Constrained Surgery", IEEE/RSJ International Conference on Intelligent Robots and Systems (IROS), 2017, pp. 174-180.

Veldman, Sebastiaanl., "Design and Analysis Methodologies for Inflated Beams", https://ui.adsabs.harvard.edu/abs/2005PhDT . . . 6V/abstract, 2005, pp. 1-174.

* cited by examiner

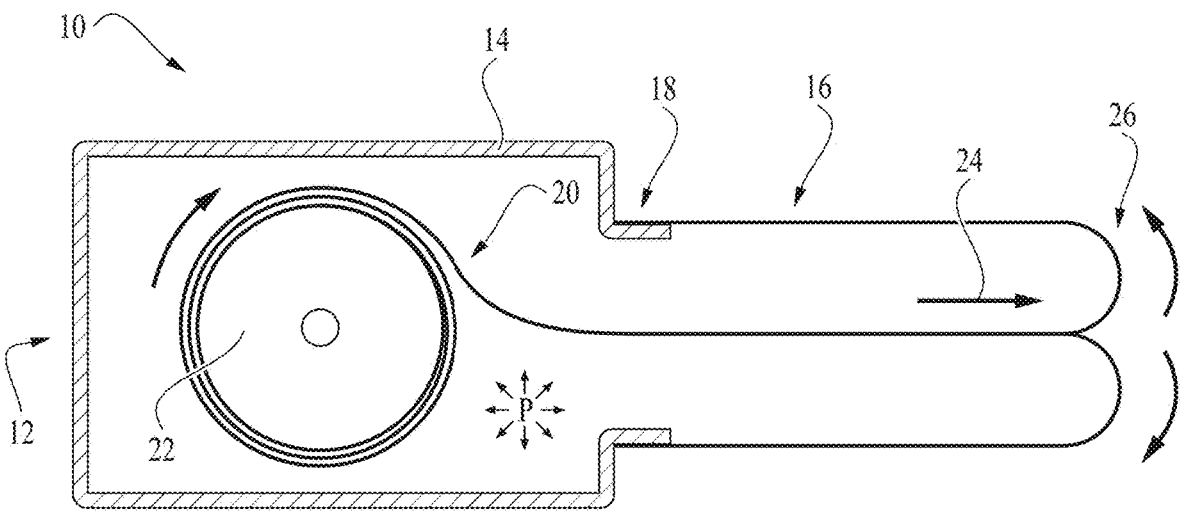
_fig. 1_
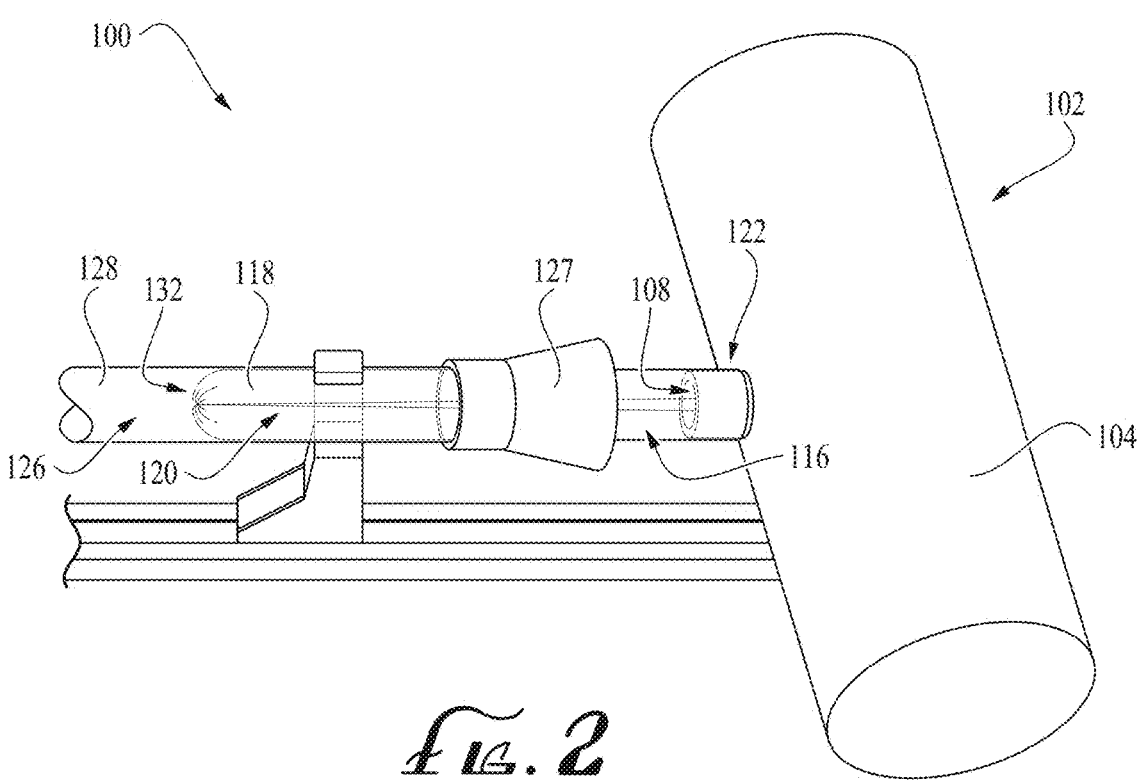
_fig. 2_

CONTROLLER $f_{IG}.5$

PASSIVE CONTROL SYSTEM FOR AN EVERTING SHEATH

CROSS REFERENCE TO RELATED APPLICATION

This application claims priority benefit under 35 U.S.C. § 119 (e) of U.S. Provisional Patent Application No. 63/537,724, filed Sep. 11, 2023, the disclosure of which is hereby incorporated by reference in its entirety.

STATEMENT OF FEDERALLY SPONSORED RESEARCH AND DEVELOPMENT

This invention was made with government support under Grant No. 2036255, awarded by the National Science Foundation. The government has certain rights in the invention.

TECHNICAL FIELD

The present disclosure relates generally to everting sheath systems. In particular, the disclosure relates to systems and methods for controlling an eversion process and for estimating a position of a leading tip of an everting sheath as the sheath transitions from a retracted position to an extended position.

BACKGROUND

Everting sheaths, or everting tube robots, are a type of growing soft robot designed for navigating arbitrary and constricted environments. In a conventional design, everting sheaths grow or elongate from a leading tip of material in response to the introduction of fluid pressure within a cavity of the sheath, wherein portions of the sheath are pulled forward from within the sheath cavity and move outwardly from the leading tip. Since the sheath material travels through the sheath cavity during expansion, the exterior surface of the sheath does not slide against the environment during growth. As such, the everting sheath or tube robot can passively self-navigate a complex environment without requiring feedback control and can also grow while causing minimal impact to the surrounding environment.

Everting sheaths or tube robots are promising in various settings, including medical applications since they can be easily introduced via a small incision or through a natural orifice of the body (e.g., transoral, transnasal, transanal, transotic, transvaginal, or transurethral approaches) and are able to navigate tortuous anatomy with minimal or no risk of additional trauma to surrounding tissues during deployment. For example, everting sheaths may be used in emergency air management, where the sheaths may be introduced into the trachea to seal the airway and restore oxygenation. In other examples, everting sheaths may be deployed into the large intestine during colonoscopies, into mammary glands for breast cancer detection, or into brain ventricles during brain surgery, among other potential medical uses. Since these access methods are minimally invasive, there is typically no need for incisions, which in turn reduces or eliminates the need for anesthesia, and may result in improved patient recovery and overall outcome.

Everting sheaths are typically made of inelastic materials to facilitate deformation under load and allow the sheath to more easily navigate sensitive or unknown environments. However, the nonlinear material properties that comprise everting sheaths also make it challenging to control and/or model a growth rate of the everting sheath, such as to estimate a position of the leading tip of the everting sheath during expansion. In other words, as the fluid pressure is increased to expand or extend the everting sheath, the eversion process may not proceed linearly—that is, the sheath may not evert from the leading tip at a substantially constant rate. Accordingly, it may be challenging to regulate the speed and growth rate of the everting sheath when pressurized, especially as the sheath extends to longer lengths. For example, in some deployment situations, the growth rate of the everting sheath may decrease or stop entirely until a certain (typically unknown) pressure is attained, at which point the everting sheath may explosively deploy at an uncontrolled high speed. In addition, a nonlinear growth rate also makes it difficult to estimate a position of the leading tip of the sheath as the eversion process continues.

SUMMARY

Various examples of everting sheath systems are described herein. An example system may include a reel that is rotatable about a rotational axis and a sheath stored on the reel, where the sheath is released from the reel as the reel rotates about the rotational axis. In some examples, the sheath may include an interior cavity extending between a first portion and an opposite second portion of the sheath, where the second portion of the sheath is stored on the reel in an inverted configuration. In such examples, the second portion of the sheath passes through the interior cavity and the first portion as the reel rotates about the rotational axis, the sheath everting from a retracted position to an extended position where the second portion of the sheath moves distally away relative to the first portion. The example system further includes a torque mechanism operable to apply a passive torque (such as a brake mechanism, a centrifugal clutch, an eddy current brake, a passive motor, or other suitable passive torque mechanisms) to the reel (such as via the axle or other component that drives the reel) to adjust a rate at which the sheath is released from the reel as the sheath everts from the retracted position to the extended position. In some examples, the system includes a pressure vessel and/or another fluid source operable to create a pressure differential within the sheath such that the sheath everts from the retracted position to the extended position.

Another example system may include a reel that is rotatable about a rotational axis and a sheath coupled to the reel, where the sheath is released from the reel as the reel rotates about the rotational axis. The sheath may include a flexible body having a first portion of the flexible body inverted into itself when in a retracted position, the flexible body including a pressure cavity defined therein, wherein when the pressure cavity is pressurized with a fluid, the first portion of the flexible body everts from the retracted position to an extended position where the inverted first portion of the flexible body extends outwardly through a leading tip at a distal end of the flexible body. The system may further include a torque mechanism operable to apply a passive torque directly or indirectly to the reel (and/or the axle that drives the reel) in a similar fashion as described above to adjust a rate at which the sheath is released from the reel as the sheath everts from the retracted position to the extended position. In some examples, the system further includes a pressure vessel having a housing with an opening extending therethrough, wherein the reel is disposed within the housing, and wherein the flexible body of the sheath extends through the opening as the flexible body everts from the retracted position to the extended position. In other examples, the passive torque applied by the torque mechanism may be based on a position of the leading tip as the flexible body everts from the retracted position to the extended position. In such examples, the system may further include one or more sensors configured to determine the position of the leading tip and communicate that determined position to the torque mechanism.

It should be understood that the foregoing summary provides certain examples further described herein and is not intended to identify any key or critical aspects of the disclosed or claimed subject matter. Further, aspects of the example systems summarized above may be combined in any suitable manner without departing from the principles of the disclosed or claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are therefore not to be considered limiting in scope, the disclosure will be described with additional specificity and detail through use of the accompanying drawings, in which:

FIG. 1 is a schematic illustration of a rotary eversion process in accordance with examples described herein.

FIG. 2 illustrates an everting sheath system in accordance with examples described herein.

DETAILED DESCRIPTION

Figure 3:
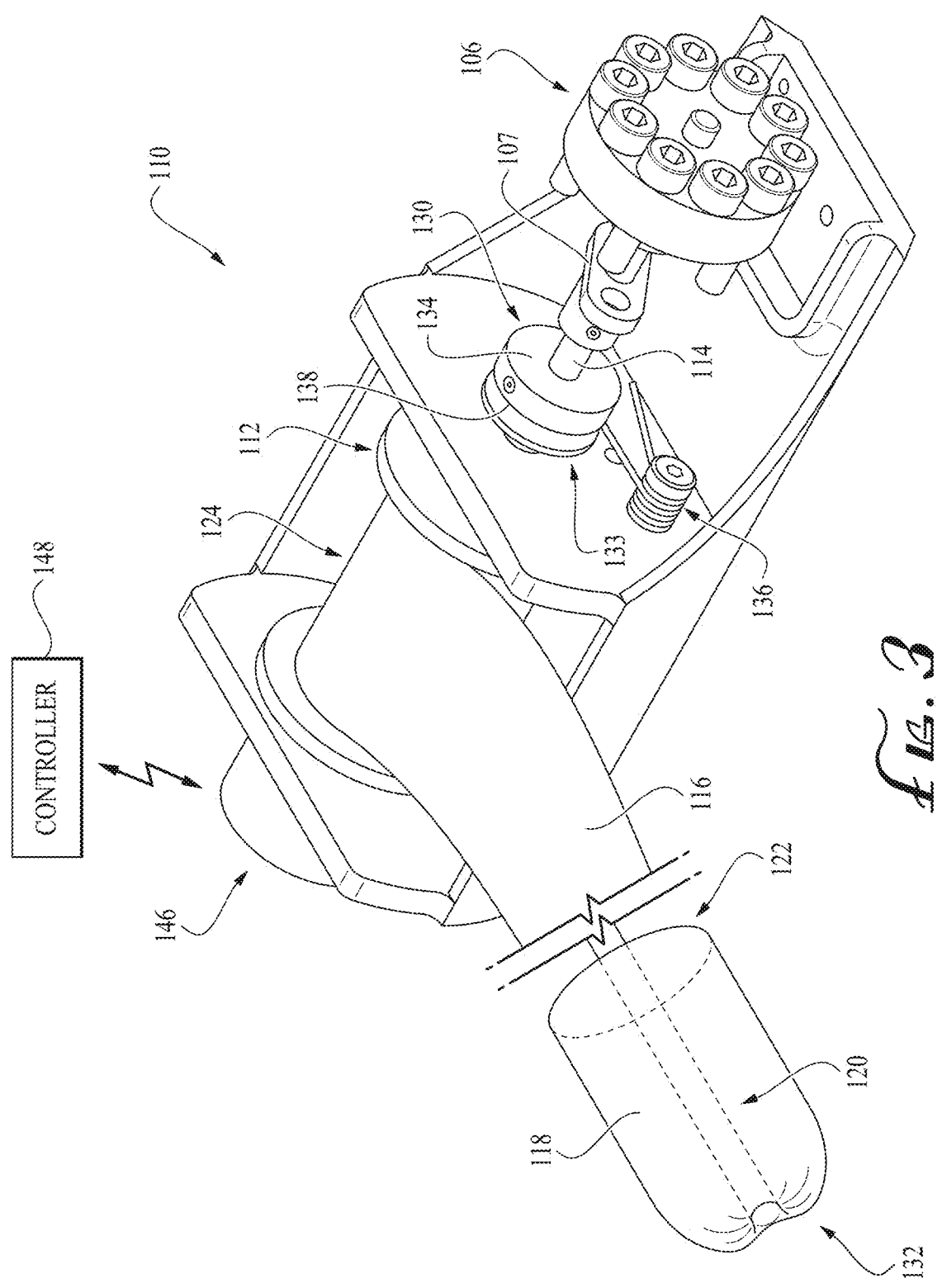
FIG. 3 illustrates an eversion reel system housed within a pressure vessel of the everting sheath system of FIG. 2 in accordance with examples described herein.
Figure 4:
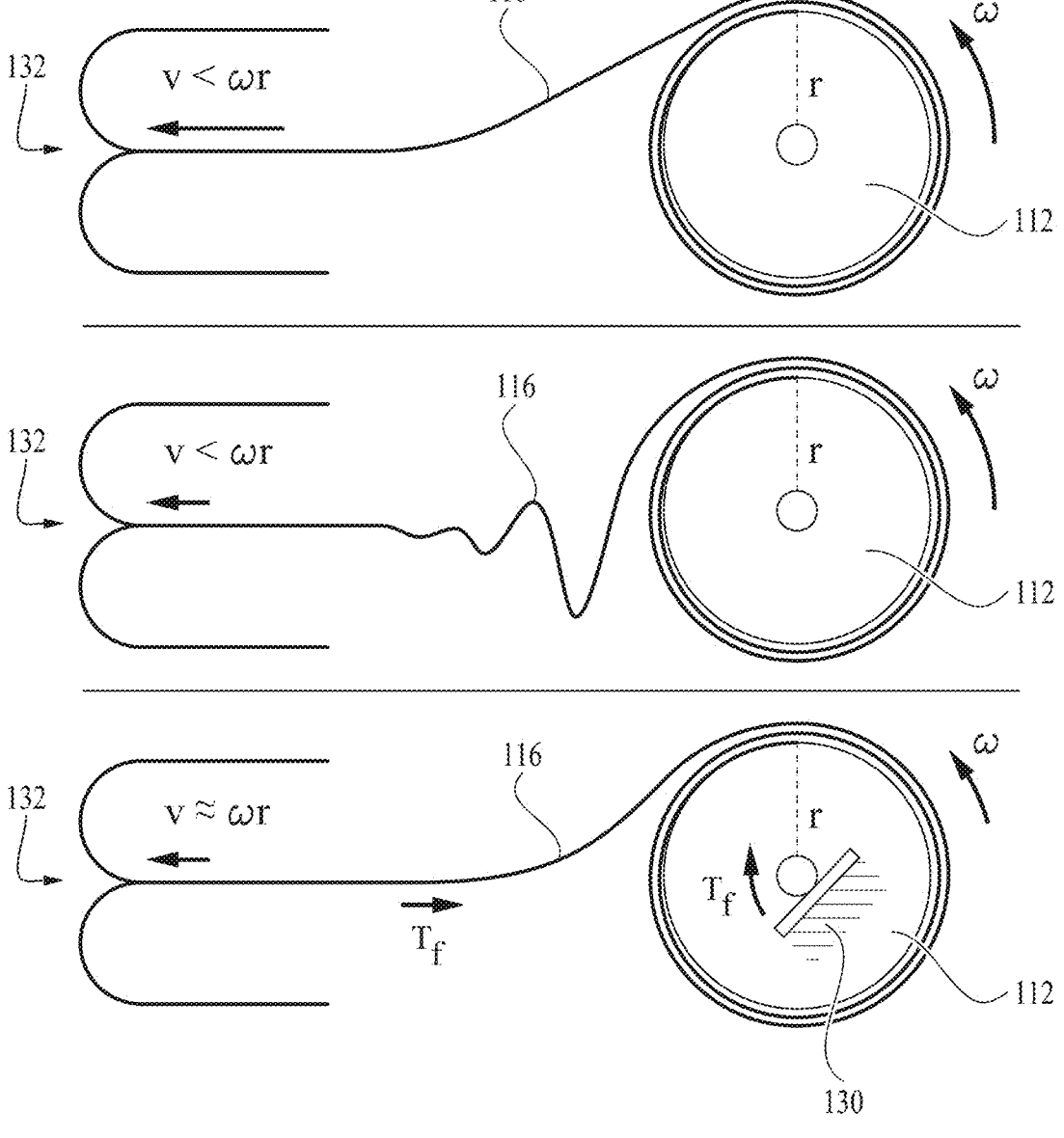
FIG. 4 is a schematic illustration depicting various release characteristics of an everting sheath from an eversion reel system in accordance with examples described herein.
Figure 5:
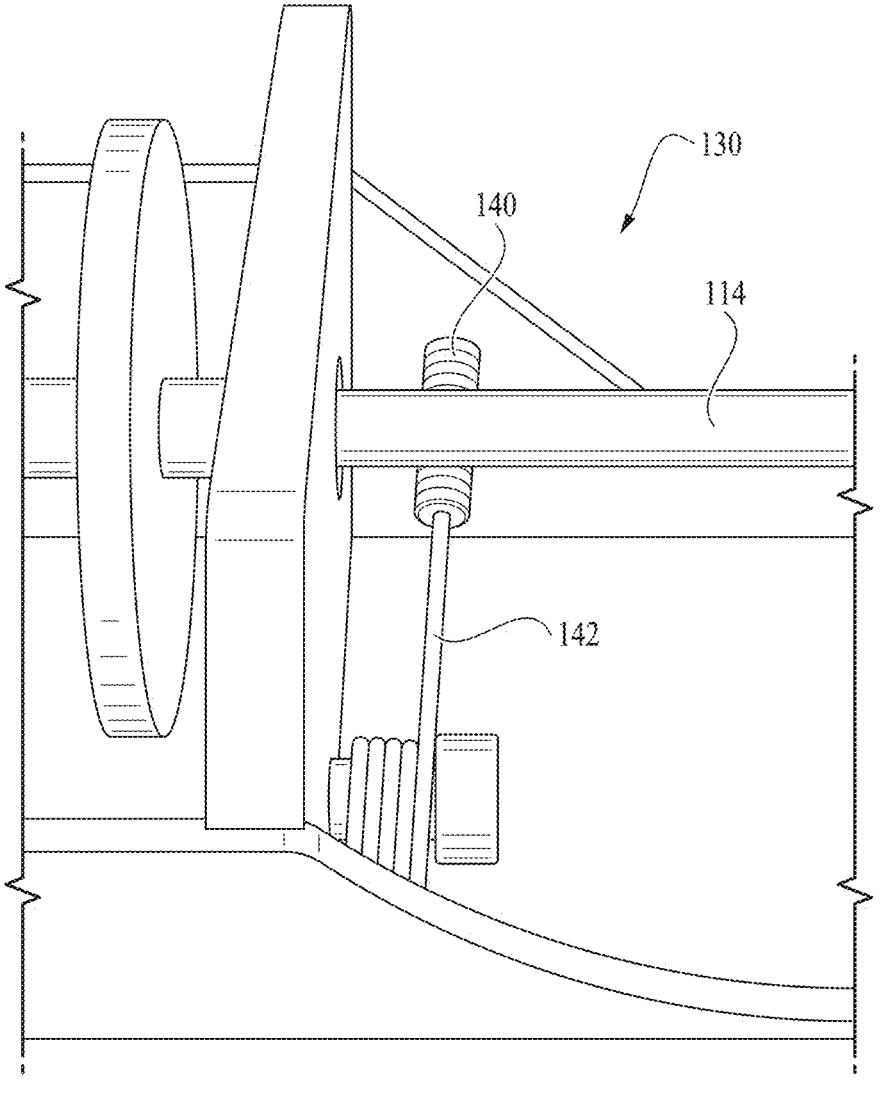
FIG. 5 illustrates an example passive torque mechanism of the everting sheath system of FIG. 2 in accordance with examples described herein.

Certain details are set forth below to provide a sufficient and clear understanding of example embodiments of the disclosure. However, it will be clear to one skilled in the art that embodiments of the disclosure may be practiced without some particular details. Moreover, the particular embodiments of the present disclosure described herein are provided by way of example and should not be used to limit the scope of the claimed subject matter to these particular embodiments. In other instances, well-known materials, components, processes, and/or anatomy have not been described or shown in detail in order to avoid unnecessarily obscuring the pertinent details of the embodiments.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

This disclosure is generally directed to everting sheath systems, such as everting tube robots, and particularly to related systems and methods for controlling expansion characteristics and for estimating a position of the leading tip of the everting sheath during the eversion process. As noted previously, in some examples, the everting sheath may be used in medical applications for delivery within tortuous human anatomy. In such medical applications, precise control of the everting sheath may help ensure that the everting sheath expands smoothly and in an expected manner so as to minimize the risk of trauma to delicate anatomy. In addition, an accurate estimate of the position of the leading tip of the sheath during the eversion process may help understand a real-time position of the everting sheath within the anatomy without the need to rely on additional sensors (e.g., time-of-flight sensors, acoustic sensors, pressure sensors, or the like) or complex imaging technologies. In some example embodiments, the estimated position information, in turn, may be used as feedback to help regulate fluid pressure and facilitate fine adjustments of the eversion process and may also be used to help determine whether the everting sheath is at a desired target position.

As described, one aim of the everting sheath system disclosed herein is to improve sheath eversion processes to more predictably control eversion of the sheath within a target environment. In some embodiments, the everting sheath system includes a sheath stored on a reel, where the reel is rotatable to release the sheath during the eversion process. The system further includes torque mechanism (such as a brake mechanism, a centrifugal clutch, an eddy current brake, a passive motor, or other suitable torque mechanisms) operable to apply a passive torque (either directly or indirectly) to the reel to adjust an angular momentum of the reel. The applied passive torque facilitates control of the rate at which the sheath is released from the reel as the sheath everts from the retracted position to the extended position. As further described in detail below, adjusting the release rate of the sheath from the reel may help provide better control of the eversion process as new sheath material everts from a leading tip of the sheath, and also aids in providing a more accurate estimate of a position of the leading tip of the sheath. Additional aspects of these and other example systems will be apparent from the following detailed description of example embodiments, which proceed with reference to the accompanying drawings.

Everting sheath systems may be used for any suitable application, primarily those that may require navigation of confined spaces and/or circuitous pathways that may include unknown features and unpredictable environments. Example uses for medical devices and related applications (e.g., endoscopy, intubation, etc.) were previously noted, but other suitable applications may include search and rescue in collapsed buildings, soil sampling, equipment inspection, electrical installation, pipe inspections, among others. It should be understood that these examples applications are provided for context and are not intended to limit the scope of the disclosure or claimed subject matter.

FIG. 1 is a simplified schematic illustration of a rotary sheath eversion process in accordance with one example. With reference to FIG. 1, the eversion system 10 includes a vessel 12 with a housing 14. A sheath 16 includes a first portion 18 that may be coupled to the housing 14 and a second portion 20 stored on a rotatable reel 22. The sheath 16 may be a thin, inelastic tube made of sheets of plastic or coated fabric or other suitable material. When stored on the reel 22, the second portion 20 of the sheath 16 is stored in an inverted configuration. In other words, the sheath 16 is arranged on the reel 22 such that it is folded inside itself. As the vessel 12 is pressurized, the sheath 16 lengthens distally outwardly of the housing 14 and along direction of motion 24, while at the same time, new sheath material that was previously inverted is pulled through the sheath 16 and everts outwardly at a leading tip 26. While the sheath 16 everts in response to fluid pressure, the reel 22 rotates about a rotational axis to controllably release the stored sheath material to aid in the eversion process.

In some examples, as the sheath 16 continues everting and the leading tip 26 moves distally away along the direction of motion 24, the nonlinear material properties of the inelastic sheath 16 may disrupt the consistency of the eversion process. For example, the sheath 16 may get stuck and cease lengthening at an expected growth rate, and then may explosively deploy once a certain (unknown) pressure has been attained. In some environments of use, such as medical applications, this unpredictable behavior may have a detrimental effect on patient outcomes and may cause trauma to surrounding tissues during use. Accordingly, a need has been identified for an improved everting sheath system designed with improved control functionalities to facilitate the eversion process and avoid these undesirable characteristics.

With collective reference to FIGS. 2-7, the following describes an everting sheath system 100, 200 designed for controlled delivery of an everting sheath 116 within a target environment of use. In some embodiments, the everting sheath system 100, 200 may also be used to more accurately estimate a position of a leading tip of the sheath through the eversion process without need for additional sensors and/or complex visual technologies.

Figure 6:
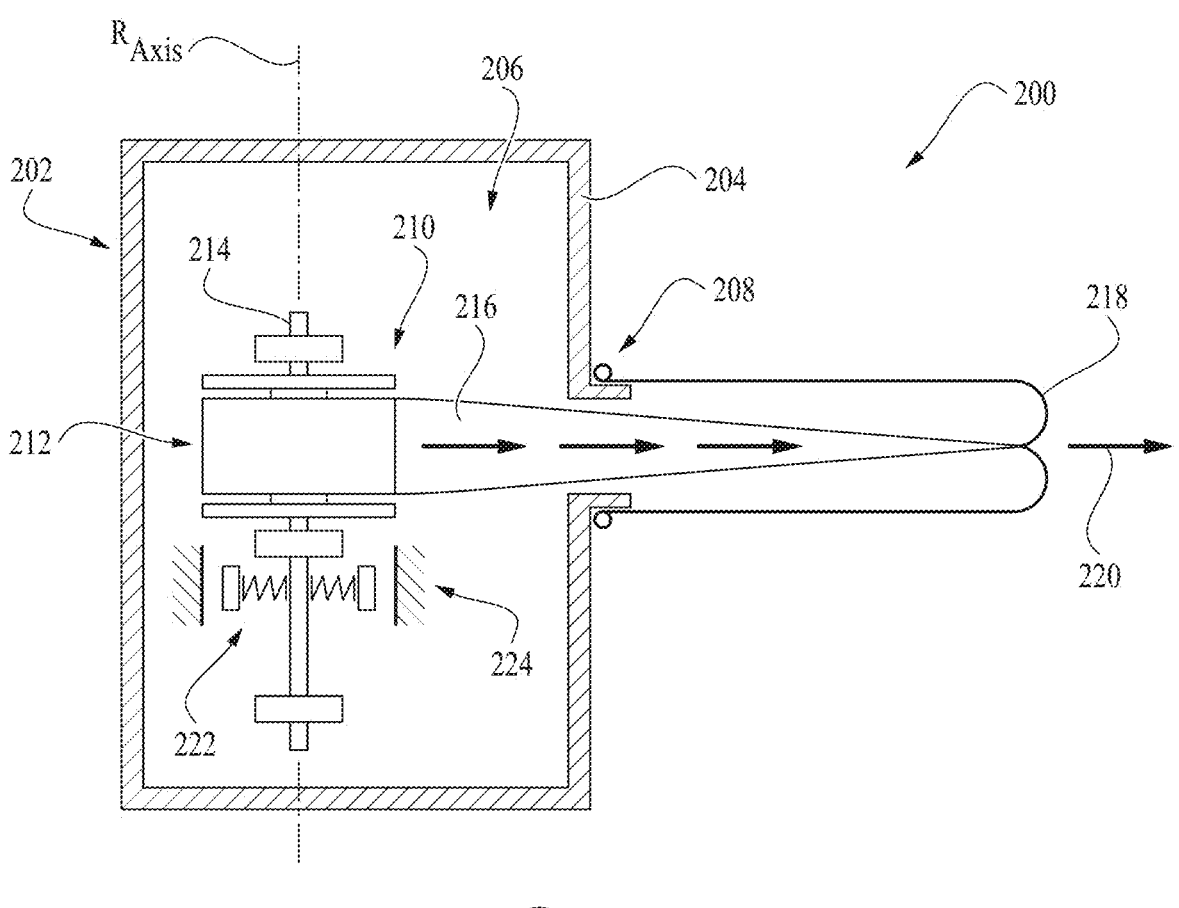
FIG. 6 is a schematic illustration of another everting sheath system in accordance with examples described herein.

FIGS. 2-3 collectively illustrate an everting sheath system 100 in accordance with examples described herein. With reference to FIG. 2, the everting sheath system 100 includes a pressure vessel 102 having a housing 104 with an interior cavity (e.g., interior cavity 206 as shown in FIG. 6) therein, and an opening 108 extending through the housing 104. Disposed within the interior cavity of the housing 104, the everting sheath system 100 includes an eversion reel system 110 as illustrated in FIG. 3. In some examples, the reel system 110 includes a reel 112 coupled to an axle 114, where the reel 112 is rotatable about a rotational axis that extends through the axle 114 (see $R_{axis}$ illustrated in FIG. 6). In some examples, the everting sheath system 100 includes a drive 106 (or other suitable motor or drive mechanism) coupled to the axle 114 and configured for adjusting the angular momentum of the reel 112 about the rotational axis.

The everting sheath system 100 further includes a sheath 116 that may be made of any suitable flexible, inelastic material, including thermoplastics (thermoplastic polyurethane, low-density polyethylene), thermosets, thermoplastic-coated fabrics, thermoset-coated fabrics, uncoated fabrics, or the like. The sheath 116 may include a flexible, tubular body 118 with an interior cavity 120 extending between a first portion 122 and an opposite second portion 124 of the flexible body 118. In one example, the second portion 124 of the sheath 116 is stored on the reel 112, where the reel 112 is configured to continuously release segments of the body 118 of the sheath 116 as the reel 112 rotates about the rotational axis. In some examples, a segment of the second portion 124 of the sheath 116 may be clamped or otherwise coupled (including a releasable coupling) to the reel 112, while in other examples the second portion 124 may be free and not coupled or otherwise affixed to the reel 112. The sheath system 100 may further include a winding knob 107 or other suitable mechanism in operable communication with the reel 112 (such as via the axle 114), where the winding knob 107 is operable to rewind the reel 112 and retract the sheath 116 back onto the reel 112 after deployment.

In one example, the second portion 124 of the sheath 116 is stored on the reel 112 in an inverted configuration such that the second portion 124 of the sheath 116 is folded within other portions of the sheath 116 in a retracted position. The sheath 116 is designed to evert from the retracted position to an extended position, wherein the second portion of the sheath 116 passes through the interior cavity and advances past the first portion 122 in response to fluid pressure applied to the interior cavity via the pressure vessel 102 as generally described with reference to FIG. 1. The pressure vessel 102 may be any suitable vessel, such as a pressurized gas tank, a pressure regulator, a pump, or the like, operable to create a pressure differential and move any suitable fluid (e.g., water or gas) from a fluid source through the sheath 116 to evert the second portion 124 from the retracted position distally outwardly and away relative to the first portion 122 to the extended position.

With reference to FIG. 2, in one configuration, the first portion 122 of the sheath 116 is coupled to the pressure vessel 102 in a non-inverted configuration, where the first portion 122 may be coupled adjacent the opening 108. As described previously, the second portion 124 of the sheath 116 may be stored on the reel 112 in an inverted configuration. When the interior cavity of the sheath 116 is pressurized, the sheath 116 everts from the retracted position to an extended position where the second portion 124 of the sheath 116 moves through the opening 108 of the pressure vessel 102 and distally away relative to the first portion 122. As described with reference to FIG. 1, the second portion 124 extends outwardly through a leading tip 132 at a distal end of the body 118 of the sheath 116. As the sheath 116 everts outwardly of the pressure vessel 102, the reel 112 rotates about the rotational axis, $R_{axis}$, to continuously release segments of the flexible body 118 and continue lengthening the everting sheath 116 beyond the first portion 122. As illustrated in FIG. 2, the sheath 116 may evert outwardly of the pressure vessel 102 into a lumen 126 of a different structure 128 (e.g., arteries or other anatomical spaces). In some embodiments, a guide funnel 127 (or other suitable guide element) may be used to help direct the everting sheath 116 into the lumen 126 of the target structure 128. In other examples, the sheath 116 may evert into other environments as noted previously in the provided use examples.

In one example, the eversion reel system 110 includes a rotary encoder 146 (such as a differential quadrature encoder or other suitable sensor systems) mounted to the reel 112 or the drive 106. The encoder 146 is capable of measuring changes in position and/or velocity associated with the reel 112. The data obtained by the encoder 146 may be used to estimate a position of the leading tip 132 of the sheath 116 during eversion. In some examples, the encoder 146 may be in operable communication with a controller 148 for receiving and/or storing the encoder data. In some embodiments, the controller 148 may be in operable communication with the drive 106 and operable to send control signals thereto for adjusting the angular momentum of the reel 112.

With reference to FIG. 3, the eversion reel system 110 includes a torque mechanism 130 operably coupled to the reel 112, where the torque mechanism 130 is operable to apply a passive torque directly or indirectly to the reel 112 to control its angular momentum and adjust a rate at which the reel 112 rotates about the rotational axis, $R_{axis}$, which in turn adjusts a rate at which the sheath 116 is released from the reel 112 as the sheath 116 everts from the retracted position to the extended position. In some embodiments, the torque mechanism 130 may be directly coupled to the reel 112, or may be indirectly coupled to the reel 112, such as via the axle 114 as shown in FIG. 3 or via the drive 106 or via other components. As illustrated in the upper schematic in FIG. 4, when the eversion velocity at the leading tip 132 of the everting sheath 116 substantially matches the linear velocity of the reel 112, the segments of the sheath 116 being released from the reel 112 will remain taut and there is a predictable relationship between the angular velocity of the reel 112 and the position of the leading tip 132 of the everting sheath 116 during the eversion process.

However, when the eversion velocity at the leading tip 132 decreases in comparison to the linear velocity of the reel 112, continued rotation of the reel 112 causes additional segments of the sheath 116 to unroll or release from the reel 112 (see center schematic in FIG. 4) and pool or cause slack in the sheath 116 adjacent the reel 112. This scenario results in a discrepancy and leads to an inaccurate measurement for the position of the leading tip 132 of the everting sheath 116. In these scenarios, the torque mechanism 130 may apply a passive torque (e.g., friction torque) to decrease the angular momentum of the reel 112 such that the linear velocity of the reel 112 is reduced to substantially match the eversion velocity at the leading tip 132. The passive torque applied (directly or indirectly) against the reel 112 decreases the rate at which the sheath 116 is released from the reel 112 to eliminate the material slack and allow the sheath 116 to become taut again (see bottom schematic in FIG. 4). In some examples, the applied passive torque will slow growth of the everting sheath 116 at the leading tip 132 to help improve the determination of the position of the leading tip 132 and make it more predictable during dynamic growth.

The torque mechanism 130 may include any suitable system operable to create a passive torque for adjusting rotation of the reel 112. For example, with reference to FIG. 4, the torque mechanism 130 may include a brake mechanism 133 operable to apply a resistance or friction torque to the reel 112 (indirectly via the axle 114 as shown in the illustrated example). The brake mechanism 133 may include a friction drum 134 coupled to the axle 114 and rotatable therewith and further include a suitable brake element, such as a biasing element 136 (e.g., a torsion spring or the like), designed to ride against a groove 138 that extends around a circumference of the friction drum 134. As the biasing element 136 rides against the groove 138, it creates a passive friction torque against the friction drum 134, which in turn reduces the angular momentum of the reel 112 via the axle 114. In another example illustrated in FIG. 5, the torque mechanism 130 may include a braking element in the form of a friction pad 140 coupled to an end of a biasing element 142, where the friction pad 140 directly contacts the axle 114 to create a passive friction torque directly against the axle 114. In another example, the friction pad 140 may instead contact the friction drum 144 to adjust the resistance applied to the axle 114, which in turn adjusts the angular momentum of the reel 112.

In another embodiment, the torque mechanism 130 may include an eddy current brake (not shown) designed to slow the axle 114 (and the reel 112) via electromagnetic forces. In one example, the eddy current brake includes a magnet (e.g., a permanent magnet or electromagnet) operable to create a magnetic field, and a conductive member (e.g., a rotating bar or disk) in operable communication with the reel 112 via the axle 114. As the conductive member moves through the magnetic field, a drag force is exerted on the conductive member and opposes its motion due to eddy currents induced in the conductive member by the magnetic field. In an electromagnetic system, the magnitude of the drag force exerted on the conductive member (and in turn, the axle 114) can be adjusted by varying the electric current in the electromagnet. The drag force exerted on the conductive member in turns slows the axle 114 and the reel 112 to control release of the sheath 116 as desired.

In some or all of the above-referenced embodiments, the torque mechanism 130 may include or may be in operable communication with a control system (not shown) that may be operable to selectively engage and disengage the brake mechanism 133 and/or to alter electric current in the eddy current brake for finely controlling adjustments of the angular momentum of the reel 112 as desired to control the eversion process. In some examples, the torque mechanism 130 may be in operable communication with the controller 148, where the controller 148 is operable to determine the passive torque that is to be applied to the reel 112 via the torque mechanism 130. In such examples, the controller 148 may directly control the torque mechanism 130, such as engaging the brake mechanism 133 to apply the determined friction torque, or may alter an electric current of the eddy brake mechanism as needed. In some embodiments, the controller 148 may base the passive torque determination on the position and/or velocity data of the reel 112 as obtained via the encoder 146.

In some examples, the everting sheath system 100 may further include one or more sensors (not shown), such as a fluid flow sensor, a pressure sensor, or an acoustic sensor, configured to determine a position of the leading tip 132 of the sheath 116. In such examples, the one or more sensors may be in operable communication with the torque mechanism 130 (and/or the controller 148) and configured to communicate the determined position of the leading tip 132 of the sheath 116 to the torque mechanism 130 (and/or the controller 148). In some examples, the torque mechanism 130 (including via the controller 148) may apply a passive torque based on the determined position of the leading tip 132 as the sheath 116 everts from the retracted position to the extended position.

Figure 7:
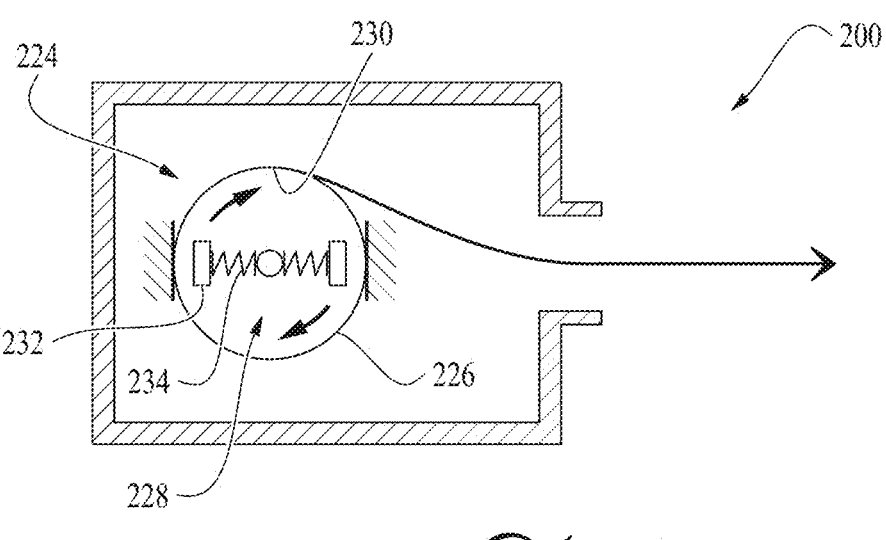
FIG. 7 is an enlarged view of a passive torque mechanism of everting sheath system of FIG. 6 in accordance with examples described herein.

FIGS. 6-7 collectively illustrate another everting sheath system 200 in accordance with examples described herein. The everting sheath system 200 includes many of the same components as the everting sheath system 100 of FIGS. 2-3 arranged in a similar manner and with similar functionality as described previously. For example, the everting sheath system 200 includes a pressure vessel 202 having a housing 204 with an interior cavity 206 therein, and an opening 208 extending through the housing 204. The everting sheath system 200 also includes an eversion reel system 210 with a reel 212 coupled to an axle 214, where the reel 212 is rotatable about a rotational axis, R$_{axis}$, that extends through the axle 214. The everting sheath system 200 further includes a sheath 216 that is substantially similar to the sheath 116 as previously described, where the sheath 216 is stored or otherwise coupled to the reel 212, and releasable therefrom as the reel 212 rotates as described previously. As illustrated in FIG. 6, the sheath 216 is designed to evert through the opening 208 in the pressure vessel 202 and extend from a leading tip 218 along the direction of motion 220 in response to fluid pressure in a similar fashion as described previously.

With reference to FIGS. 6-7, the everting sheath system 200 further includes a torque mechanism 222 operably coupled to the reel 212 (via the axle 214), the torque mechanism 222 operable to directly or indirectly apply a passive torque to the reel 212 to adjust a rate at which the sheath 216 is released from the reel 212 as the sheath 216 everts from the retracted position to the extended position. In some examples, the torque mechanism 222 includes a centrifugal clutch system 224. The centrifugal clutch system 224 includes a brake drum 226 coupled to the axle 214, and rotatable therewith about the rotational axis, R$_{axis}$. With reference to FIG. 7, the brake drum 226 includes an interior cavity 228 and an interior wall 230 facing the interior cavity 228. The centrifugal clutch system 224 includes one or more brake elements 232 (e.g., weighted brake shoes, brake pads, or other suitable elements) disposed within the interior cavity 228 of the brake drum 226, where each of the brake elements 232 is coupled to a respective biasing element 234. Both the brake elements 232 and the biasing elements 234 are rotatable with the brake drum 226. In operation, the one or more brake elements 232 move toward the interior wall 230 of the brake drum 226 via the one or more biasing elements 234 as the axle 214 (and the reel 212) rotates about the rotational axis, R$_{axis}$. As the brake drum 226 rotates faster, the brake elements 232 move closer to the interior wall 230 and eventually contact the interior wall 230 to apply a passive torque (e.g., friction) to control rotation of the reel 212 (such as via the axle 214). In some examples, the brake drum 226 helps ensure that the axle 214 (and the reel 212) do not freely rotate beyond a predetermined velocity. Once the rotation reaches the predetermined velocity, the brake drum 226 applies a passive torque to help regulate rotation of the reel 212.

In other examples, the torque mechanism of the everting sheath systems 100, 200 may instead include a motor operable to generate a passive torque. In some examples, including the passive torque mechanisms 130, 222 described in the prior examples, the torque mechanisms 130, 222 may apply a passive torque that is proportional to an angular velocity of the reel 112, 212 such that the sheath 116, 216 everts from the retracted position to the extended position at a substantially constant rate to help minimize the potential for explosive growth. In still other examples, an everting sheath system may incorporate a vacuum chamber in place of a pressure vessel, and the sheath may evert from the retracted position to the extended position within the vacuum chamber.

It should be understood that example embodiments provided herein of both the design of the everting sheath systems and any potential use applications associated therewith are not intended to be limiting. Other configurations of the everting sheath systems, as well as different use applications that would benefit from the use of the disclosed subject matter, are possible and encompassed within the scope of the disclosure. In addition, it is to be appreciated that any one of the above embodiments or processes, or specific features associated therewith, may be combined with one or more other embodiments and/or processes or be separated and/or performed amongst separate devices or device portions in accordance with the present systems, devices, and methods. Further, while some advantages associated with certain embodiments of the disclosure may have been described in the context of these embodiments, other embodiments may also exhibit such advantages or may exhibit different advantages. It should be understood that not all embodiments need necessarily exhibit such advantages to fall within the scope of the claimed subject matter.

Finally, the disclosure is intended to be merely illustrative of the present devices, apparatuses, systems, and methods and should not be construed as limiting the appended claims to any particular embodiment or group of embodiments. Thus, while the present disclosure has been described in particular detail with reference to exemplary embodiments, it should also be appreciated that numerous modifications and alternative embodiments may be practiced without departing from the broader and intended spirit and scope of the present disclosure as set forth in the claims that follow. Accordingly, the specification and drawings are to be regarded in an illustrative manner and are not intended to limit the scope of the appended claims.

The invention claimed is:

1. An everting sheath system comprising:

a reel rotatable about a rotational axis;

a sheath having an interior cavity extending between a first portion and an opposite second portion of the sheath, wherein the second portion of the sheath is stored on the reel in an inverted configuration, and wherein the second portion of the sheath passes through the interior cavity and the first portion as the reel rotates about the rotational axis, the sheath everting from a retracted position to an extended position where the second portion of the sheath moves distally away relative to the first portion; and a torque mechanism operably coupled to the reel, the torque mechanism operable to directly or indirectly apply a passive torque to the reel to adjust a rate at which the sheath is released from the reel as the sheath everts from the retracted position to the extended position.

2. The everting sheath system of claim 1, further comprising a fluid source in operable communication with the sheath, wherein the fluid source creates a pressure differential to evert the sheath from the retracted position to the extended position.

3. The everting sheath system of claim 1, further comprising a pressure vessel housing the reel, and wherein the first portion of the sheath is coupled to the pressure vessel in a non-inverted configuration, and wherein the second portion of the sheath extends outwardly of the pressure vessel as the sheath everts from the retracted position to the extended position.

4. The everting sheath system of claim 1, wherein the torque mechanism includes a brake mechanism operable to apply a resistance torque to the reel.

5. The everting sheath system of claim 4, wherein the brake mechanism includes an eddy current brake comprising:
   a magnet operable to generate a magnetic field; and
   a conductive member in operable communication with the reel, wherein the conductive member moves through the magnetic field of the magnet, and wherein the magnetic field exerts a drag force on the conductive member to adjust a rotational motion of the conductive member.

6. The everting sheath system of claim 4, wherein the torque mechanism includes a brake mechanism with a brake element, the brake element movable to contact the reel and adjust an angular velocity thereof.

7. The everting sheath system of claim 4, wherein the torque mechanism includes a centrifugal clutch comprising:
   a drum rotatable about a second rotational axis, the drum in operable communication with the reel, the drum including an interior cavity and an interior wall facing the interior cavity;
   one or more brake elements disposed within the interior wall of the drum; and
   one or more biasing elements coupled to the one or more brake elements, wherein the one or more brake elements move toward the interior wall of the drum via the one or more biasing elements as the reel rotates about the rotational axis, the one or more brake elements contacting the drum and applying the passive torque to control rotation of the reel.

8. The everting sheath system of claim 4, wherein the torque mechanism includes a motor, the motor operable to generate the passive torque.

9. The everting sheath system of claim 1, wherein the passive torque applied via the torque mechanism is proportional to an angular velocity of the reel such that the sheath everts from the retracted position to the extended position at a constant rate.

10. The everting sheath system of claim 1, wherein the second portion of the sheath is releasably coupled to the reel.

11. The everting sheath system of claim 1, further comprising a vacuum chamber housing the reel and the sheath, and wherein the sheath everts from the retracted position to the extended position within the vacuum chamber.

12. The everting sheath system of claim 1, further comprising:
   a sensor operable to obtain sensor data associated with the reel, the sensor data including one or both of a position and a velocity of the reel; and
   a controller in communication with the torque mechanism, the controller configured to determine the passive torque directly or indirectly applied to the reel via the torque mechanism based on the sensor data.

13. The everting sheath system of claim 1, further comprising a drive operably coupled to the reel, the drive configured to rotate the reel about the rotational axis.

14. The everting sheath system of claim 13, wherein the torque mechanism is coupled to the drive and operable to apply the passive torque to the drive.

15. An everting sheath system comprising:
   a reel rotatable about a rotational axis;
   a sheath coupled to the reel, the sheath including a flexible body having a portion of the flexible body inverted into itself when in a retracted position, the flexible body including an interior cavity defined therein, wherein when the interior cavity is pressurized with a fluid, the portion of the flexible body everts from the retracted position to an extended position where the inverted portion of the flexible body extends outwardly through a leading tip at a distal end of the flexible body; and
   a torque mechanism operably coupled to the reel, the torque mechanism operable to directly or indirectly apply a passive torque to the reel to adjust a rate at which the sheath is released from the reel as the sheath everts from the retracted position to the extended position.

16. The everting sheath system of claim 15, further comprising a pressure vessel having a housing with an opening extending therethrough, wherein the reel is disposed within the housing, and wherein the flexible body of the sheath extends through the opening as the flexible body everts from the retracted position to the extended position.

17. The everting sheath system of claim 15, further comprising a fluid source in operable communication with the sheath, wherein the fluid source pressurizes the interior cavity of the sheath.

18. The everting sheath system of claim 15, wherein the passive torque applied by the torque mechanism is based on a position of the leading tip as the flexible body everts from the retracted position to the extended position.

19. The everting sheath system of claim 18, further comprising one or more sensors configured to determine the position of the leading tip, wherein the one or more sensors is in operable communication with the torque mechanism and configured to communicate the determined position of the leading tip to the torque mechanism.

20. The everting sheath system of claim 19, wherein the one or more sensors includes one or more of a fluid flow sensor, a pressure sensor, or an acoustic sensor.

* * * * *